United States Patent [19]

Dawkins, Jr.

[11] Patent Number: 5,258,785
[45] Date of Patent: Nov. 2, 1993

[54] CLOSE-VIEW DATA DISPLAY IMPLANT FOR SPORTING EYEWEAR

[76] Inventor: Douglas R. Dawkins, Jr., 434 Arguello Blvd., San Francisco, Calif. 94118

[21] Appl. No.: 720,355

[22] Filed: Jun. 25, 1991

[51] Int. Cl.⁵ .............................................. G02C 1/00
[52] U.S. Cl. ...................................... 351/43; 351/57; 351/158
[58] Field of Search ........................ 351/43, 158, 57; 358/108; 359/630

[56] References Cited

U.S. PATENT DOCUMENTS

| | | | |
|---|---|---|---|
| 4,751,691 | 6/1988 | Perera | 351/158 |
| 4,796,987 | 9/1989 | Linden | 351/158 |
| 4,867,551 | 9/1989 | Perera | 351/158 |

Primary Examiner—Rodney B. Bovernick
Assistant Examiner—Hung Xuan Dang
Attorney, Agent, or Firm—B. Noel Kivlin

[57] ABSTRACT

An eyewear apparatus for use in sporting activities allows convenient view and control of a data display device by an athlete. A data display implant device including a data display and a lens is incorporated in association with sporting eyewear such as a pair of swimming goggles. The data display implant device may be an integral unit of the eyewear or may be a retrofit unit. A motion sensitive switch may also be included to cause freezing of the display device following each flip-turn of the swimmer. In addition, a radio transmitter and receiver may be used to control the data display device.

17 Claims, 2 Drawing Sheets

CLOSE-VIEW DATA DISPLAY IMPLANT FOR SPORTING EYEWEAR

BACKGROUND OF THE INVENTION

1. Field Of The Invention

The present invention relates to visual display devices for displaying data in association with sporting activities.

2. Description Of The Relevant Art

A common problem encountered by athletes while participating in sports is their inability to conveniently monitor data such as time—both the time of day and the passage of an elapsed time. In some cases, visual access to and control of a timing device is impossible. An example of this problem occurs when an athlete participates in the sport of swimming. Competitive swimmers must use timing devices to determine how fast they are going and to manage their training. Such timing devices are typically either small hand-held units or larger wall-mounted units. Unfortunately, these athletes are unable to continuously view the timers while swimming and are therefore required to either stop or modify their activity to get a reading of time. This requirement is inconvenient and results in inaccurate readings. Furthermore, precise measurement of lap-time while swimming from end-to-end of the swimming pool can be difficult.

The problem of visual access to and accurate control of timing and other data displaying devices also exists in other sports, such as snow-skiing and triathlon. It is therefore desirable to provide a data display device that can be conveniently viewed and controlled by an athlete.

SUMMARY OF THE INVENTION

An eyewear apparatus for use with sporting activities in accordance with the present invention allows convenient view and control of a data display device by an athlete. The eyewear apparatus includes a data display implant device having a data display means and a lens. The data display implant device may be incorporated within sporting eyewear such as a pair of swimming goggles and may be an integral unit of the eyewear or may be a retrofit unit. A motion sensitive switch may also be included to cause pausing of the display device following each flip-turn of the swimmer. In addition, a radio transmitter and receiver may be used to control the data display means.

In accordance with one aspect of the invention, the eyewear apparatus includes a transparent eye shield, means for supporting the eye shield near a person's eyes to allow viewing of objects through the eye shield, a data display means mounted adjacent to the eye shield for displaying information, and a lens optically positioned to allow viewing of the data display means through the lens.

The eyewear apparatus may further comprise a mirror optically positioned between the lens and the data display means and a timing circuit coupled to the data display means. In one embodiment, the lens is a Fresnel lens. In yet another embodiment, a motion sensitive switch is coupled to the timing circuit to cause automatic control of the timing circuit upon the occurrence of a particular movement of the athlete.

In accordance with a further aspect of the invention, swimming goggles are provided comprising a transparent eye cover, means for supporting the transparent eye cover near the athlete's eyes to allow vision therethrough, the means for supporting the transparent cover providing a substantially water-tight seal between the athlete's face and the transparent eye cover. The swimming goggles further comprise a data display means mounted adjacent to the transparent eye cover and a lens optically positioned to allow vision of the data display means through the lens.

In accordance with a final aspect of the invention, a data display implant for connection to sporting eyewear comprises a housing unit connectable to the eyewear, a data display means mounted within the housing, and a lens optically positioned to allow viewing of the timing display.

The invention will be more readily understood by reference to the drawings and the detailed description. As will be appreciated by one skilled in the art, the invention is applicable to data display devices used in association with sporting eyewear in general, and is not limited to the specific embodiment disclosed.

DETAILED DESCRIPTION

The following includes a detailed description of the best presently contemplated mode for carrying out the invention. The description is intended to be merely illustrative of the invention and should not be taken in a limiting sense.

Figure 1:
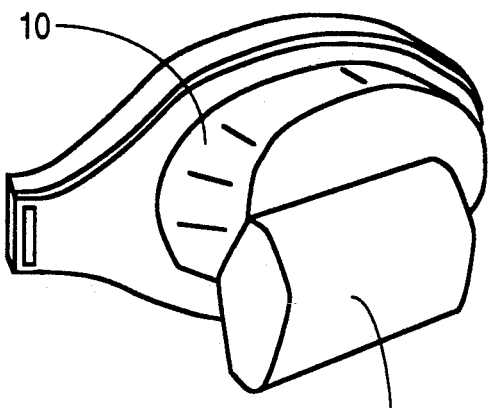
FIG. 1 shows a perspective view of a swimming goggle with a data display implant in accordance with the invention.

A first embodiment of a sporting eyewear apparatus incorporating a data display in accordance with the present invention is described in conjunction with FIGS. 1-4. FIG. 1 shows a perspective view of the right-side eyepiece portion 10 of a pair of swimming goggles including a data display implant 12 attached thereto. In this particular embodiment, the data display implant 12 is secured as a retrofit to a pair of conventionally available swimming goggles.

The conventional pair of swimming goggles includes transparent eye covers. As used herein, the term transparent means having the property of passing light without appreciable scattering so that objects beyond are entirely visible. Therefore, the transparent eye covers may be clear or tinted.

Figure 2:
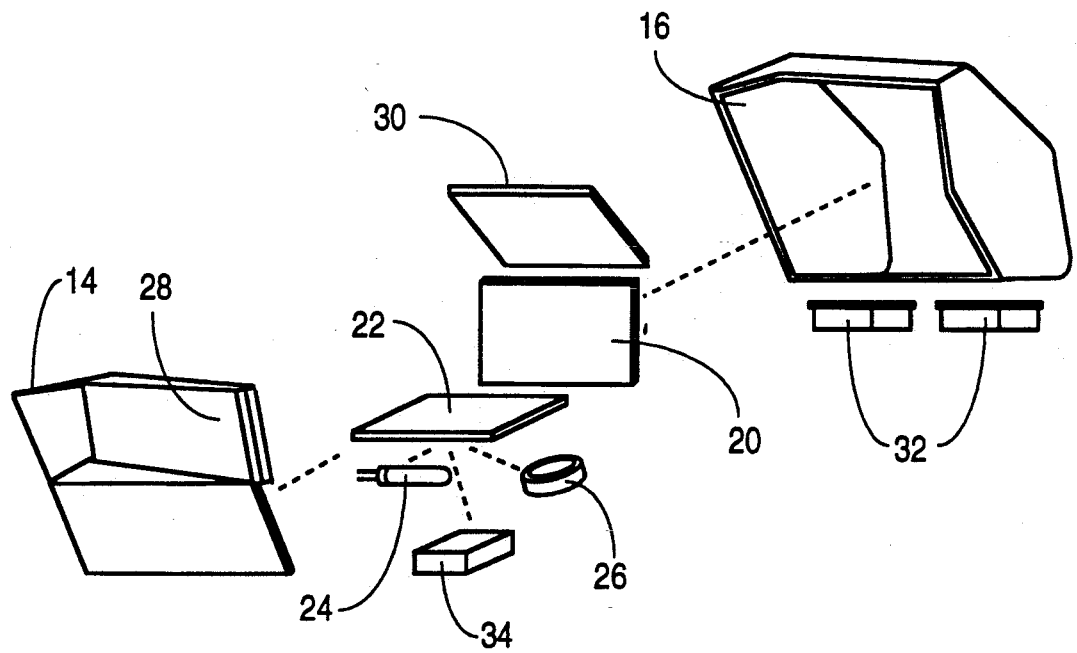
FIG. 2 shows an exploded parts diagram of the data display implant.

FIG. 2 shows an explosion view of the data display implant 12. The data display implant 12 comprises a watertight housing manufacturable by injection molding clear plastic. The housing includes a front portion 14 and a back portion 16. Protrusions within the front portion 14 of the housing allow for positioning and mounting of the data display implant 12 on the goggle eyepiece 10. The data display implant 12 is attached to the pair of swimming goggles such that the housing obscures only the lower portion of one goggle eyepiece.

The data display implant 12 comprises several primary components within the housing 14, 16. Referring to FIG. 2, the data display implant 12 comprises a timing device 20 such as a timer IC (integrated circuit), a display device 22 such as an alphanumeric LCD (liquid crystal display) screen which may be incorporated in association with an illuminator 24 such as an LED (light emitting diode), and a battery 26 to power the timer IC 20, display device 22 and illuminator 24. The data display implant 12 further comprises a lens 28 such as a flat, grooved, acrylic lens commonly known as a Fresnel lens to allow extremely close viewing of the display device 22, and a mirror 30 which allows greater flexibility in the physical relationship associated with the eye, the lens 28 and the display device 22.

Figure 3:
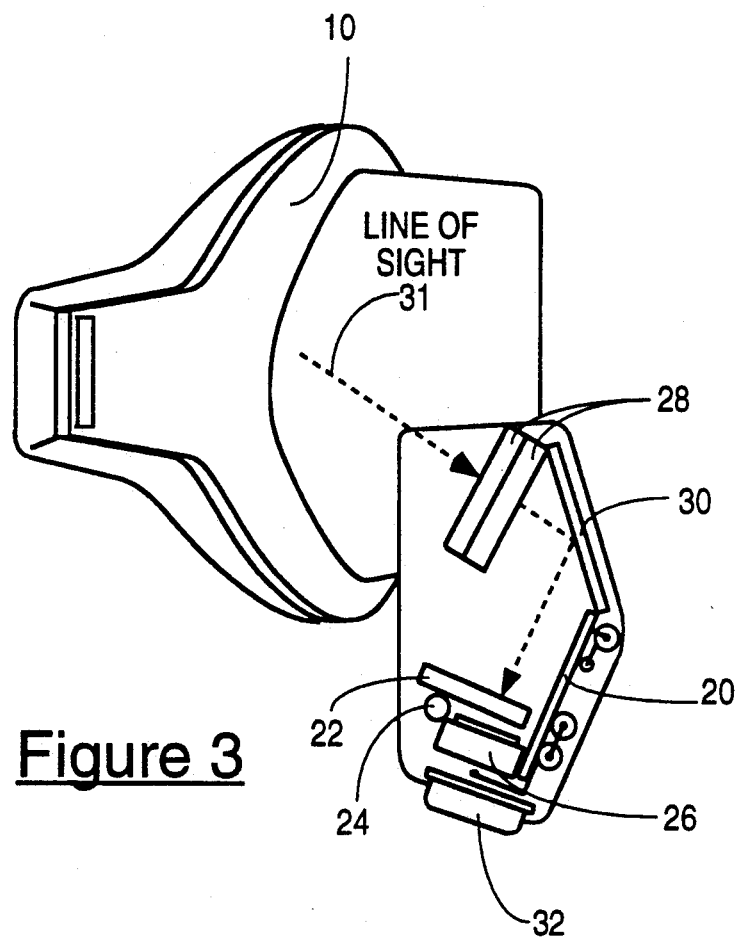
FIG. 3 shows the swimming goggle with a data display implant illustrating the athlete's line of sight.

The lens is mounted on or molded into the surface of the front portion 14 of the housing. The distance from the cornea of the wearer's eye to the closest plane of the lens 28 is typically from 6 to 17 millimeters. As shown in FIG. 3, the lens 28 is positioned such that the line of sight of the wearer passes through the lens 28 in a substantially perpendicular direction with respect to the plane of the lens 28 when the wearer views the display device 22. The mirror 30 is positioned behind the lens 28 (approximately 6 millimeters) and is angled with its plane at approximately 45 degrees with respect to the line of sight. The display device 22 is positioned approximately 13 millimeters below the mirror 30 with its display facing upward. The wearer's line of sight 31 therefor passes through the lens 28 and is reflected downward by the mirror 30 to allow optical viewing of the upward facing display device 22. The timer IC 20 and battery 26 are mounted below the display device 22. The timer IC 20 may be mounted to a printed circuit board which also mounts associated components, such as resistors. Controls 32 such as push buttons protrude through the back portion 16 of the housing for the purpose of allowing the wearer to start and stop the timer IC 20 and to change modes between elapsed time (stopwatch) and time-of-day.

The data display implant 12 incorporated in association with the pair of swimming goggles may further include a motion sensitive switch 34 such as a mercury switch which pauses the updating of the display device 22 when activated (closed). The switch 34 as incorporated within this embodiment is particularly useful in the sport of swimming since it is operatively coupled to the timer IC 20 and to the display device 22 such that the display device 22 freezes (does not change) momentarily after each flip-turn by the swimmer, allowing easier and more accurate viewing of lap times while the athlete continues to swim.

It is noted that the use of a Fresnel lens 28 allows for a reduction in both the size and weight of the required lens and, because of its reduced thickness, allows for greater distance between the eye and the lens 28 and between the lens 28 and the mirror 30 and/or display device 22. This greater clearance allows for more flexibility in design and greater safety to the wearer.

It is also noted that the reflecting of the line of sight 31 due to the mirror 30 allows for greater flexibility in creating a more compact and more streamlined housing.

It is furthermore noted that only a limited area of view is obstructed due to the data display implant 12. Therefore, the user has a near-normal range of vision when not reading the implant. The user can easily view the display device 22 by looking downward—similar to the process utilized by bifocal eyeglass wearers.

Figure 4:
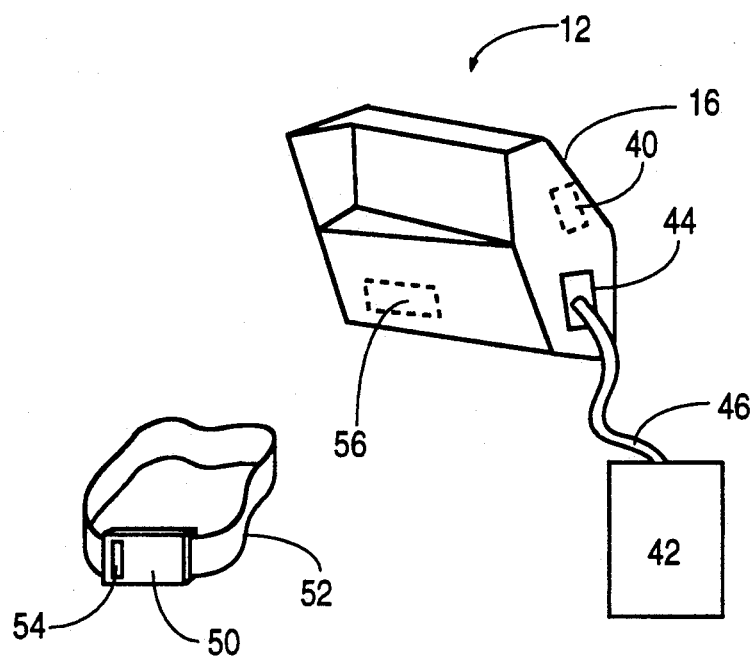
FIG. 4 shows a diagram of the swimming goggle with a data display implant including a computer processor, receiver and transmitter.

Referring next to FIG. 4, the close-view data display implant for sporting eyewear according to the present invention may further be used in association with an electronic data storage and retrieval system. The electronic data storage and retrieval system includes a memory IC 40 and a computer processor 42. A connector 44 is attached to the back portion 16 of the housing to allow connection of the memory IC 40 to the computer processor 42 through a cable 46. The data storage and retrieval system is adapted such that the memory IC 40 is coupled to the timing device 20 to allow for the initial storage of timing data, such as lap-times, while the athlete is swimming. The memory IC 40 may be incorporated as an integral component of the timing device 20. After completion of swimming, the athlete connects the cable 46 to the connector 44 to allow down-loading of data from the memory IC 40 to the computer processor 42. The timing data is thereby available for further analysis and long-term storage within the computer processor 42. As an alternative to the cable 46, a contact reader may be used which extracts information via a contact established between a small metal plate on the data display implant 12 and a similar plate on the reader. Such a contact reader is similar to that used within Polar brand name wrist heart rate monitors.

A further embodiment of the invention includes a miniature radio frequency transmitter 50 having a push-button control 54 and fitted in an elastic band 52 which may be worn on the index finger similar to a ring. The push-button 54 can be activated by bringing the thumb of the same hand into contact with the device. Activation of the transmitter sends a signal to a receiver 56 within the data display implant 12. This signal starts and stops the timer IC 20 and controls the timer IC 20 in much the same way as the motion switch 34 except that the radio frequency transmitter 50 allows greater flexibility in controlling the device.

A variation of the radio transmitter 50 and receiver 56 system may also be used to display alphanumeric information from an outside source on the display device 22. In such a system, the receiver 56 mounted within the data display implant 12 receives signals generated by an outside transmitter 50 and converts the signals for display on the display device 22. The transmitter 50 could be controlled, for example, by the athlete's coach or by a computer. This system is useful to the athlete in that it allows discreet communication of instructions or data concerning externalities which are not readily apparent to the athlete.

It is further noted that the battery 26 may be rechargeable and coupled to the connector 44 for connection to an external power source.

The data display implant may further be implemented in eyewear suitable for snow-skiing, jogging or running, triathlon, bicycling, and nearly any other activity wherein access to data is a concern of the athlete. The data display implant may further be incorporated in association with conventional sunglasses for use with leisure sporting activities.

In addition, the housing of the data display implant 12 may be integrated in association with sporting eyewear as a single unit rather than as a retrofit.

It is finally noted that the timing IC 20 may include processing means to display internally or externally generated alphanumeric data.

Numerous modifications and variations will become apparent to those skilled in the art once the above disclosure is fully appreciated. It is to be understood that the above detailed description of the preferred embodiment is intended to b merely illustrative of the spirit and scope of the invention and should not be taken in a limiting sense. The scope of the claimed invention is better defined with reference to the following claims.

What is claimed is:

1. An eyewear apparatus for use in conjunction with sporting activities comprising:
   a transparent eye shield;
   means for supporting said eye shield near a person's eyes to allow viewing of objects through said eye shield;
   a data display means mounted adjacent to said eye shield for displaying information; and
   a flat Fresnel lens optically positioned to allow viewing of said data display means through said flat Fresnel lens.

2. The eyewear apparatus as recited in claim 1 further comprising a mirror optically positioned between said lens and said data display means.

3. The eyewear apparatus as recited in claim 1 further comprising a timing circuit coupled to said data display means.

4. The eyewear apparatus as recited in claim 3 further comprising a timing memory couple to said timing circuit for storing timing data.

5. The eyewear apparatus as recited in claim 4 further comprising connector means coupled to said timing memory, said connector means being adapted to allow transfer of data from said timing memory to an external processor.

6. An eyewear apparatus for use in conjunction with sporting activities comprising:
   a transparent eye shield;
   means for supporting said eye shield near a person's eyes to allow viewing of objects through said eye shield;
   a data display means mounted adjacent to said eye shield for displaying information;
   a lens optically positioned to allow viewing of said data display means through said lens;
   a timing circuit coupled to said data display means; and
   a motion sensitive switch coupled to said timing circuit.

7. Swimming goggles to be worn by an athlete comprising:
   a transparent eye cover;
   means for supporting said transparent eye cover near the athlete's eyes to allow vision therethrough, said means for supporting said transparent eye cover allowing a substantially water-tight seal between the athlete's face and said transparent eye cover;
   a data display means mounted adjacent to said transparent eye cover; and
   a flat Fresnel lens optically positioned to allow vision of said data display means through said flat Fresnel lens.

8. The eyewear apparatus as recited in claim 7 further comprising a mirror optically positioned between said flat Fresnel lens and said data display means.

9. The eyewear apparatus as recited in claim 7 further comprising a timing circuit coupled to said data display means.

10. The eyewear apparatus as recited in claim 9 further comprising a timing memory coupled to said timing circuit for storing timing data.

11. The eyewear apparatus as recited in claim 10 further comprising connector means coupled to said timing memory, said connector means being adapted to allow transfer of data from said timing memory to an external processor.

12. Swimming goggles to be worn by an athlete comprising:
   a transparent eye cover;
   means for supporting said transparent eye cover near the athlete's eyes to allow vision therethrough, said means for supporting said transparent eye cover allowing a substantially water-tight seal between the athlete's face and said transparent eye cover;
   a data display means mounted adjacent to said transparent eye cover;
   a lens optically positioned to allow vision of said data display means through said lens;
   a timing circuit coupled to said data display means; and
   a motion sensitive switch coupled to said timing circuit.

13. The eyewear apparatus as recited in claim 12 wherein said motion sensitive switch causes said timing display to pause when the swimmer makes a flip-turn.

14. An eyewear apparatus device comprising a data display implant said eyewear apparatus further comprising:
   a housing unit connected to said eyewear apparatus;
   a timing data display means mounted within said housing unit; and
   a flat Fresnel lens optically positioned to allow viewing of said timing display through said flat Fresnel lens.

15. The eyewear apparatus as recited in claim 14 further comprising a mirror optically positioned between said flat Fresnel lens and said data display means.

16. An eyewear apparatus device comprising a data display implant said eyewear apparatus further comprising:
   a housing unit connected to said eyewear apparatus;
   a data display means mounted within said housing unit;
   a lens optically positioned to allow viewing of said timing display through said lens; and
   a motion sensitive switch coupled to said data display means.

17. An eyewear apparatus device comprising a data display implant said eyewear apparatus further comprising:
   a housing unit connected to said eyewear apparatus;
   a data display means mounted within said housing unit;
   a lens optically positioned to allow viewing of said timing display through said lens; and
   a radio-frequency receiver coupled to said data display means for receiving signals transmitted from an external transmitter and for converting said signals to alphanumeric information for display on said data display means.

* * * * *